(12) United States Patent
Ragini et al.

(10) Patent No.: US 8,017,787 B2
(45) Date of Patent: Sep. 13, 2011

(54) ORGANOMETALLIC COMPLEX AND ORGANIC ELECTROLUMINESCENCE DEVICE USING THE SAME

(75) Inventors: Das Rupasree Ragini, Suwon-si (KR); Che-Un Yang, Suwon-si (KR); Young-Hun Byun, Yongin-si (KR); O-Hyun Kwon, Seoul (KR); Lyong-Sun Pu, Suwon-si (KR); Jong-Jin Park, Yongin-si (KR); Byoung-Ki Choi, Hwaseong-si (KR); Hee-Kyung Kim, Anyang-si (KR); Myeong-Suk Kim, Suwon-si (KR)

(73) Assignee: Samsung Mobile Display Co., Ltd., Giheung-Gu, Yongin, Gyunggi-Do (KR)

( * ) Notice: Subject to any disclaimer, the term of this patent is extended or adjusted under 35 U.S.C. 154(b) by 818 days.

(21) Appl. No.: 11/640,418

(22) Filed: Dec. 18, 2006

(65) Prior Publication Data
US 2007/0176542 A1     Aug. 2, 2007

(30) Foreign Application Priority Data
Jan. 27, 2006   (KR) .................. 10-2006-0009013

(51) Int. Cl.
C07F 15/00    (2006.01)
H01J 1/62     (2006.01)
H01J 63/04    (2006.01)

(52) U.S. Cl. .............. 548/101; 313/504; 546/2
(58) Field of Classification Search .......... 313/504; 548/101; 546/2
See application file for complete search history.

(56) References Cited

U.S. PATENT DOCUMENTS

| 2003/0152802 A1 | 8/2003 | Tsuboyama et al. |
| 2004/0124766 A1 | 7/2004 | Nakagawa et al. |
| 2005/0119485 A1 | 6/2005 | Brown et al. |
| 2005/0175860 A1 | 8/2005 | Kim et al. |
| 2007/0178332 A1 | 8/2007 | Ragini et al. |
| 2007/0196689 A1 | 8/2007 | Ragini et al. |

FOREIGN PATENT DOCUMENTS

| CN | 1474826 A | 2/2004 |
| CN | 1626540 A | 6/2005 |
| JP | 2004-174838 | * 6/2004 |

OTHER PUBLICATIONS

M. A. Baldo et al., "Excitonic singlet-triplet ratio in a semiconducting organic thin film", Physical Review B, vol. 60, No. 20, pp. 14 422-140428, Nov. 15, 1999.
M. A. Baldo et al., "Highly efficient phosphorescent emission from organic electroluminescent devices", Nature, vol. 395, Sep. 10, 1998, pp. 151-154.
S. Sprouse, et al., "Photophysical Effects of Metal-Carbon σ Bonds in Ortho-Metalated Complexes of Ir(III) and Rh(III)", J. Am. Chem. Soc. 1984, 106, 6647-6653.
F. O. Garces et al., "Synthesis, Structure, Electrochemistry, and Photophysics of methyl-Substituted Pheylpyridine Ortho-Metalated Iridium(III) Complexes", Inorg. Chem. 1988, 27, 3464-3471, which was cited in the Information Disclosure Statement filed on Dec. 18, 2006 of the related U.S. Appl. Nos. 11/640,289 and 11/640,330.
Chinese Office Action issued by Chinese Patent Office on Jan. 26, 2011 corresponding to Korean Patent Application No. 2006-0016278 and Request for Entry of the Accompanying Office Action attached herewith.(Cited in the corresponding cross-referenced application No. 11/640,289 in Information Disclosure Statement filed on Apr. 15, 2011.).

* cited by examiner

*Primary Examiner* — Joseph Kosack
(74) *Attorney, Agent, or Firm* — Robert E. Bushnell, Esq.

(57) ABSTRACT

Provided are an organometallic complex providing highly efficient phosphorescence and an organic electroluminescence device using the same. The organometallic complex can be used to form an organic layer of the organic electroluminescence device, efficiently emits light of a wavelength corresponding to red light, and has high brightness and low operating voltage.

10 Claims, 2 Drawing Sheets

ORGANOMETALLIC COMPLEX AND ORGANIC ELECTROLUMINESCENCE DEVICE USING THE SAME

CROSS-REFERENCE TO RELATED PATENT APPLICATION AND CLAIM OF PRIORITY

This application claims the benefit of Korean Patent Application No. 10-2006-0009013, filed on Jan. 27, 2006, in the Korean Intellectual Property Office, the disclosure of which is incorporated herein in its entirety by reference.

BACKGROUND OF THE INVENTION

1. Field of the Invention

The present invention relates to an organometallic complex and an organic electroluminescence device, and more particularly, to an organometallic complex enabling red light emission and an organic electroluminescence device including an organic layer formed of the organometallic complex.

2. Description of the Related Art

Organic electroluminescent (EL) devices, which are active display devices, use the recombination of electrons and holes in a fluorescent or phosphorescent organic compound thin layer (hereinafter, referred to as 'organic layer') to emit light when current is applied thereto. Organic electroluminescent devices are lightweight, have wide viewing angles, produce high-quality images, and can be manufactured using simple processes. Organic electroluminescent devices also can produce moving images with high color purity while having low consumption power and low voltage. Accordingly, organic electroluminescent devices are suitable for portable electronic applications.

In general, an organic electroluminescent device includes an anode, a hole transport layer, an emission layer, an electron transport layer, and a cathode sequentially stacked on a substrate. The hole transport layer, the light emitting layer, and the electron transport layer are organic layers formed of organic compounds. The organic electroluminescent device may operate as follows. When a voltage is applied between the anode and the cathode, holes emitted by the anode move to the light-emitting layer via the hole transport layer. Electrons are emitted by the cathode and move to the light emitting layer via the electron transport layer. In the light-emitting layer, the carriers recombine to produce excitons. The excitons radiatively decay, emitting light corresponding to a band gap of the light-emitting layer.

Materials that can be used to form the light-emitting layer of the organic electroluminescent device are divided, according to the emission mechanism, into fluorescent materials using singlet excitons and phosphorescent materials using triplet excitons. The light-emitting layer is formed by such fluorescent materials or phosphorescent materials themselves or by doping such fluorescent materials or phosphorescent materials on appropriate host materials. When electrons are excited, singlet excitons and triplet excitons are generated in a host in the generation ratio of 1:3 (Baldo, et al., Phys. Rev. B, 1999, 60, 14422).

When fluorescent materials are used to form the light-emitting layer in the organic electroluminescent device, triplet excitons that are generated in the host cannot be used. However, when phosphorescent materials are used to form the light emitting layer, both singlet excitons and triplet excitons can be used, and thus, an internal quantum efficiency of 100% can be obtained (Baldo et al., Nature, Vol. 395, 151-154, 1998). Accordingly, the use of phosphorescent materials brings higher light emitting efficiency than use of fluorescent materials.

When a heavy metal, such as Ir, Pt, Rh, or Pd is included in an organic molecule, spin-orbit coupling occurs due to a heavy atom effect, and thus, singlet states and triplet states become mixed, allowing forbidden transitions to occur and thus effectively emitting light produced by a phosphorescent effect even at room temperature.

As described above, transition metal compounds that include a transition metal such as Iridium (Ir) and platinum (Pt) have been developed to provide highly efficient phosphorescent materials that use a phosphorescence effect emitting RGB colors. However, development of red phosphorescent materials for full-color display devices is still required.

SUMMARY OF THE INVENTION

The present invention provides an organometallic complex that can efficiently emit light of a wavelength corresponding to red light.

The present invention also provides an organic electroluminescence device using the organometallic complex.

According to an aspect of the present invention, there is provided an organometallic complex comprising a compound represented by Formula 1:

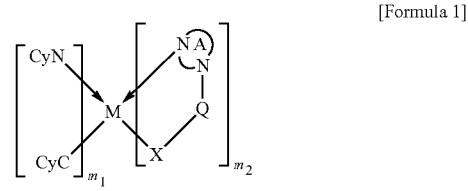

[Formula 1]

where M is Ir, Os, Pt, Pb, Re, Ru or Pd;

CyN is a substituted or unsubstituted $C_3$-$C_{60}$ heterocyclic group including nitrogen, which is coordinated with M, or a substituted or unsubstituted $C_3$-$C_{60}$ heteroaryl group including nitrogen, which is coordinated with M;

CyC is a substituted or unsubstituted $C_4$-$C_{60}$ cyclic group including carbon, which is coordinated with M, a substituted or unsubstituted $C_3$-$C_{60}$ heterocyclic group including carbon, which is coordinated with M, a substituted or unsubstituted $C_3$-$C_{60}$ aryl group including carbon, which is coordinated with M, or a substituted or unsubstituted $C_3$-$C_{60}$ heteroaryl group including carbon, which is coordinated with M;

CyN-CyC represents a cyclometalating ligand, which is coordinated with M through nitrogen (N) and carbon (C);

$m_1$ is an integer in a range of 0 to 2;

$m_2$ is 3-$m_1$;

A is a ligand including at least two nitrogen atoms and is combined with M through one of the two nitrogen atoms;

X is $NR_0$, O, or S, where $R_0$ is hydrogen, a halogen atom, a carboxyl group, or a $C_1$-$C_{20}$ alkyl group; and Q is a substituted or unsubstituted $C_6$-$C_{30}$ arylene group.

The compound represented by Formula 1 may be represented by Formula 2:

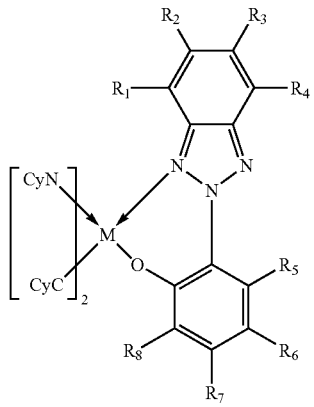

[Formula 2]

where M, CyN, and CyC are defined as in claim 1 above; and $R_1$, $R_2$, $R_3$, $R_4$, $R_5$, $R_6$, $R_7$, and $R_8$ are each independently hydrogen, a halogen atom, a carboxyl group, an amino group, a nitro group, a cyano group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{30}$ aryl group, a substituted or unsubstituted $C_7$-$C_{30}$ arylalkyl group, a substituted or unsubstituted $C_5$-$C_{30}$ heteroaryl group, a substituted or unsubstituted $C_3$-$C_{30}$ heteroarylalkyl group, or a substituted or unsubstituted $B(Ra)_2$ (Ra is hydrogen, a halogen atom, a $C_1$-$C_{20}$ alkyl group, a $C_6$-$C_{30}$ aryl group, a $C_5$-$C_{30}$ heteroaryl group, a $C_1$-$C_{20}$ alkoxy group or a $C_6$-$C_{30}$ aryloxy group), and at least two of $R_1$, $R_2$, $R_3$, $R_4$, $R_5$, $R_6$, $R_7$, and $R_8$ may be fused into a 2 to 5-membered fused ring.

The compound represented by Formula 1 may be represented by Formulae 3 through 6.

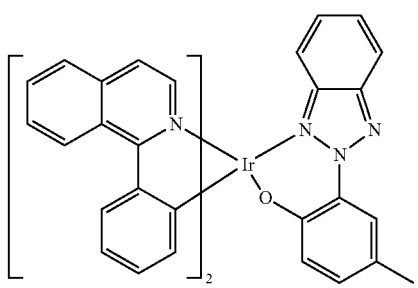

[Formula 3]

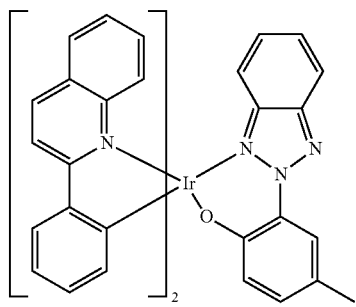

[Formula 4]

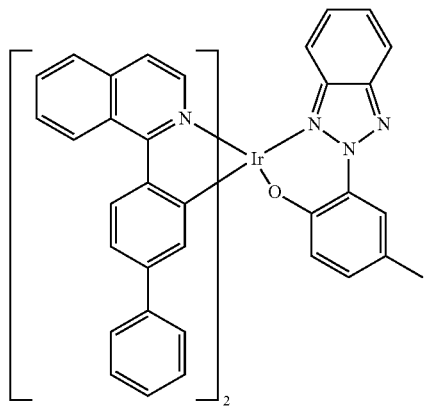

[Formula 5]

[Formula 6]

According to another aspect of the present invention, there is provided an organic electroluminescence device having an organic layer interposed between a pair of electrodes, the organic layer including an organometallic complex described above.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1A:
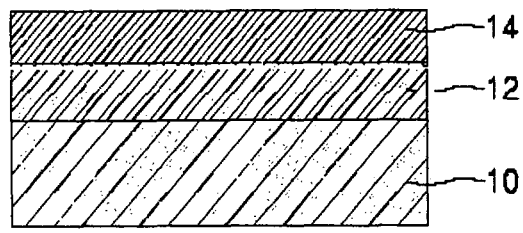
FIGS. 1a through 1f are diagrams schematically illustrate various laminated structures of an organic electroluminescent device according to embodiments of the present invention.

Hereinafter, embodiments of the present invention will be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art.

An embodiment of the present invention provides an organometallic complex comprising a compound represented by Formula 1, which includes an ancillary ligand preferably formed from a triazole derivative. The ligand in such an organometallic complex reduces an energy gap between highest occupied molecular orbital (HOMO) and triplet metal-to-ligand charge-transfer ($^3$MLCT) state to move a corresponding light emission wavelength a number of nm towards a wavelengths corresponding to red light. Accordingly light emission and color coordinate control of red light are available in the organic electroluminescent device. The organometallic complex comprising a compound represented by Formula 1 according to an embodiment of the present invention is shown:

<Formula 1>

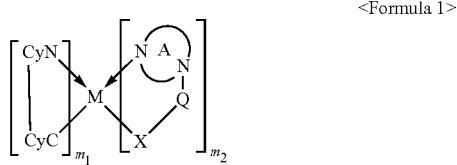

where M is Ir, Os, Pt, Pb, Re, Ru or Pd;

CyN is a substituted or unsubstituted $C_3$-$C_{60}$ heterocyclic group including nitrogen, which is coordinated with M, CyC is a substituted or unsubstituted $C_4$-$C_{60}$ cyclic group including carbon, which is coordinated with M, a substituted or unsubstituted $C_3$-$C_{60}$ heterocyclic group including carbon, which is coordinated with M, a substituted or unsubstituted $C_3$-$C_{60}$ aryl group including carbon, which is coordinated with M, or a substituted or unsubstituted $C_3$-$C_{60}$ heteroaryl group including carbon, which is coordinated with M;

CyN-CyC represents a cyclometalating ligand, which is coordinated with M through the nitrogen (N) of the CyN and the carbon (C) of the CyC;

$m_1$ is an integer in a range of 0 to 2;

$m_2$ is 3-$m_1$;

A is a ligand including at least two nitrogen atoms and is combined with M through one of the two nitrogen atoms;

X is $NR_0$, O, or S, where $R_0$ is hydrogen, a halogen atom, a carboxyl group, or a $C_1$-$C_{20}$ alkyl group; and Q is a substituted or unsubstituted $C_6$-$C_{30}$ arylene group.

In the organometallic complex of Formula 1 according to an embodiment of the present invention, M is a core metal which combines with the cyclometalating ligand or an ancillary ligand. For example, M may be Ir, Os, Pt, Pb, Re, Ru or Pd. Preferably, Ir or Pt may be used, but the core metal used is not limited thereto.

CyN of Formula 1 is a heterocyclic group or a heteroaryl group including a nitrogen atom, which directly forms a coordinate covalent bond with a core metal, M. The heterocyclic group has a cyclic group in which one or more atoms of the ring are an element other than carbon, for example, N, O, S and/or P. Examples of the substituted or unsubstituted $C_3$-$C_{60}$ heterocyclic group are pyrrolidine, morpholine, thiomorpholine, thiazolidine, and the like, but are not limited thereto. The heteroaryl has an aryl group in which one or more atoms of the ring are an element other than carbon, for example, N, O, S and/or P. Examples of the substituted or unsubstituted $C_3$-$C_{60}$ heteroaryl group are pyridine, 4-methoxypyridine, quinoline, pyrrole, indole, pyrazine, pyrazole, imidazole, pyrimidine, quinazoline, thiazole, oxazole, triazine, 1,2,4-triazole, and the like, but are not limited thereto.

Examples of the substituted or unsubstituted $C_4$-$C_{60}$ cyclic group including carbon which is combined with M in CyC of Formula 1 are cyclohexane, cyclopentane, and the like. Examples of the substituted or unsubstituted $C_3$-$C_{60}$ heterocyclic group including carbon which is combined with M may be tetrahydrofuran, 1,3-dioxane, 1,3-dithiane, 1,3-dithiolane, 1,4-dioxa-8-azaspiro[4,5]decane, 1,4-dioxaspiro[4,5]decan-2-one, and the like. Examples of the substituted or unsubstituted $C_4$-$C_{60}$ aryl group including carbon which is combined with M are phenyl, 1,3-benzodioxole, biphenyl, naphthalene, anthracene, azulene, and the like. Examples of the substituted or unsubstituted $C_3$-$C_{60}$ heteroaryl group including carbon which is combined with M are thiophene, furan2(5H)-furanone, pyridine, coumarin, imidazole, 2-phenylpyridine, 2-benzothiazole, 2-benzooxazole, 1-phenylpyrazole, 1-naphthylpyrazole, 5-(4-methoxyphenyl)pyrazole, 2,5-bisphenyl-1,3,4-oxadilzole, 2,3-benzofuran2-(4-biphenyl)-6-phenyl benzoxazole, and the like.

CyN and CyC of CyN-CyC in Formula 1 may be connected to each other to form a condensed ring such as a substituted or unsubstituted 4-7 atom ring group or a substituted or unsubstituted $C_4$-$C_7$ atom heterocyclic group. Here, a ring group or a heterocyclic group refers to a $C_1$-$C_{30}$ cycloalkyl group, a $C_1$-$C_{30}$ heterocycloalkyl group, a $C_6$-$C_{30}$ aryl group, or a $C_4$-$C_{30}$ heteroaryl group and can be substituted by one or more substituent. The term 'hetero' indicates heteroatoms such as N, O, P, S, and the like.

Examples of the substituent are a halogen atom, —$OR_1$, —$N(R_1)_2$, —$P(R_1)_2$, —$POR_1$, —$PO_2R_1$, —$PO_3R_1$, —$SR_1$, —$Si(R_1)_3$, —$B(R_1)_2$, —$B(OR_1)_2$, —$C(O)R_1$, —$C(O)OR_1$, —$C(O)N(R_1)$, —CN, —$NO_2$, —$SO_2$, —$SOR_1$, —$SO_2R_1$, and —$SO_3R_1$, where $R_1$ is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group.

X is $NR_0$, O, or S, where $R_0$ is hydrogen, a halogen atom, a carboxyl group, or a $C_1$-$C_{20}$ alkyl group.

Q is a substituted or unsubstituted $C_6$-$C_{30}$ arylene group.

$m_1$ may be an integer in the range of 0 to 2 and $m_2$ may be 3-$m_1$, preferably, $m_1$ is 1 or 2 and $m_2$ is 1 or 2, respectively. More preferably, $m_1$ is 2 and $m_2$ is 1.

A includes at least two nitrogen atoms wherein the ligand is combined with M through one of the two nitrogen atoms. Examples of A may be derived from at least one selected from the group consisting of substituted or unsubstituted indazole, substituted or unsubstituted imidazole, substituted or unsubstituted imidazoline, substituted or unsubstituted imidazolyl, substituted or unsubstituted imidazole derivative, substituted or unsubstituted pyrazole, substituted or unsubstituted benzotriazole, substituted or unsubstituted benzothiadiazole, substituted or unsubstituted oxadiazole, substituted or unsubstituted thiadiazole, substituted or unsubstituted pyrazoline, substituted or unsubstituted pyrazolidine, substituted or unsubstituted benzimidazole, and substituted or unsubstituted triazole, but are not limited thereto.

A may be one selected from the group consisting of triazole, imidazole, pyrazole, and derivatives thereof; for example, A may be derived from triazole.

The cyclometalating ligand (CyN-CyC) may be represented by one of Formulas 11 through 40, but is not limited thereto.
[Formula 11]
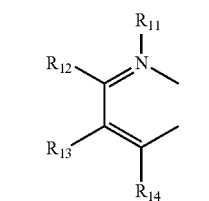
[Formula 12]
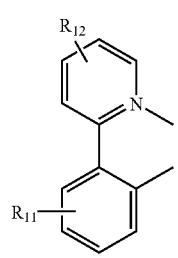
[Formula 13]
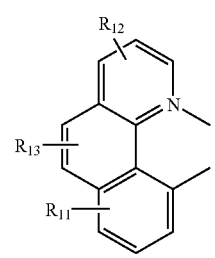
[Formula 14]
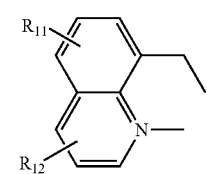
[Formula 15]
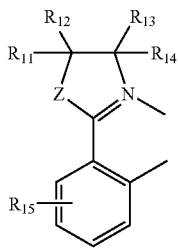
[Formula 16]
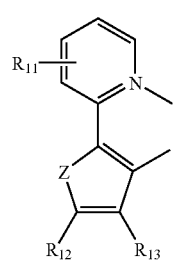
[Formula 17]
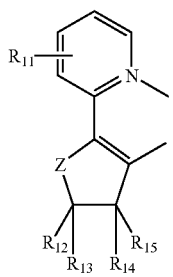
[Formula 18]
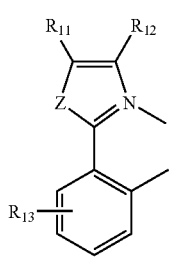
[Formula 19]
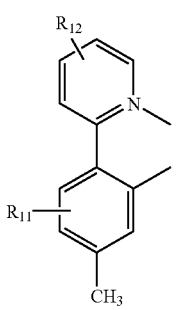
[Formula 20]
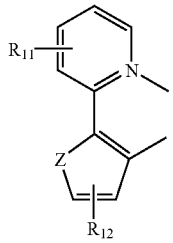
[Formula 21]
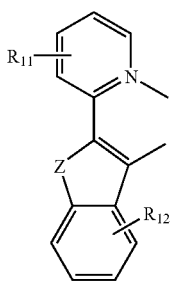

[Formula 22]
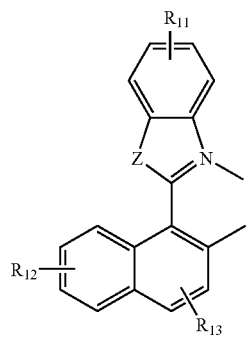
[Formula 23]
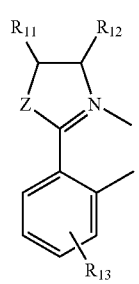
[Formula 24]
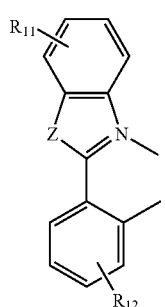
[Formula 25]
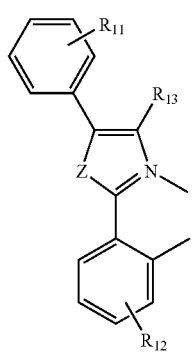
[Formula 26]
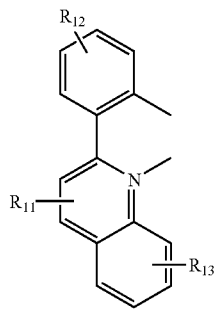
[Formula 27]
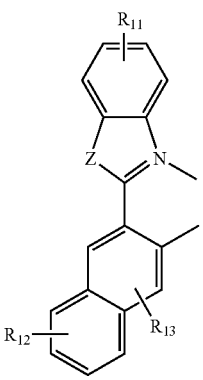
[Formula 28]
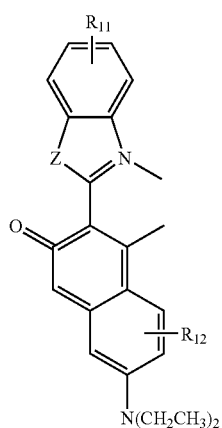
[Formula 29]
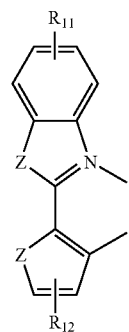
[Formula 30]
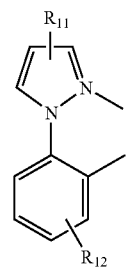

[Formula 31]
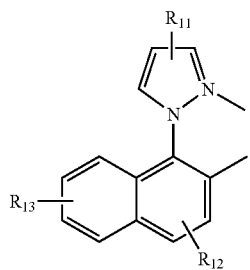

[Formula 32]
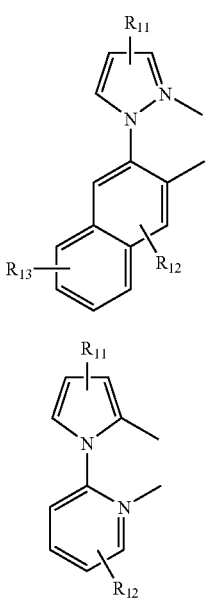

[Formula 33]

[Formula 34]
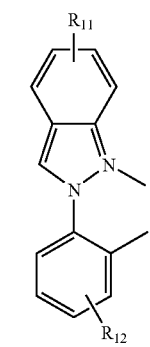

[Formula 35]
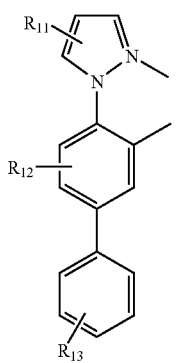

[Formula 36]
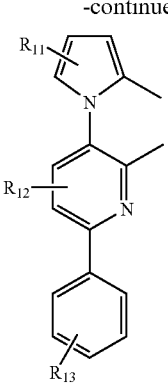

[Formula 37]
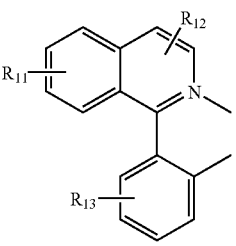

[Formula 38]
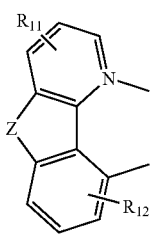

[Formula 39]
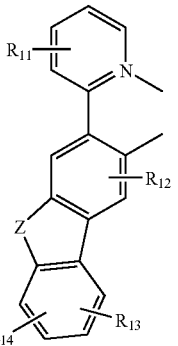

[Formula 40]
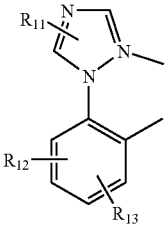

where $R_{11}$, $R_{12}$, $R_{13}$, $R_{14}$, and $R_{15}$, are each independently hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, or a $C_6$-$C_{20}$ aryl group, where R is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group and a substituted or unsubstituted $C_3$-$C_{40}$ heteroarylalkyl group; and Z is S, O, or $NR_0$, where $R_0$ is hydrogen or a $C_1$-$C_{20}$ alkyl group.

Preferably, the organometallic complex represented by Formula 1 may be represented by Formula 2.

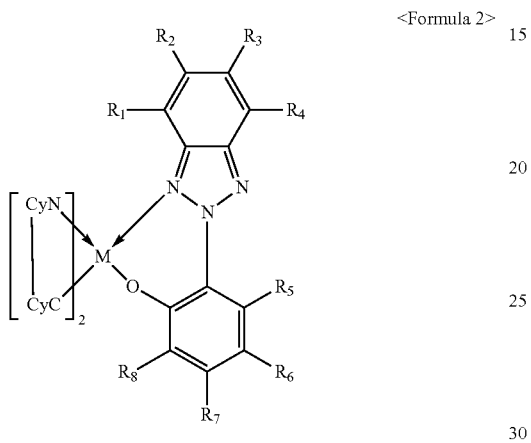

<Formula 2> where M, CyN, and CyC are defined as in the previous embodiment represented by Formula 1 above; and $R_1$, $R_2$, $R_3$, $R_4$, $R_5$, $R_6$, $R_7$, and $R_8$ are each independently hydrogen, a halogen atom, a carboxyl group, an amino group, a nitro group, a cyano group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{30}$ aryl group, a substituted or unsubstituted $C_7$-$C_{30}$ arylalkyl group, a substituted or unsubstituted $C_5$-$C_{30}$ heteroaryl group, a substituted or unsubstituted $C_3$-$C_{30}$ heteroarylalkyl group, or a substituted or unsubstituted $B(Ra)_2$ (Ra is hydrogen, a halogen atom, a $C_1$-$C_{20}$ alkyl group, a $C_6$-$C_{30}$ aryl group, a $C_5$-$C_{30}$ heteroaryl group, a $C_1$-$C_{20}$ alkoxy group or a $C_6$-$C_{30}$ aryloxy group), and at least two of $R_1$, $R_2$, $R_3$, $R_4$, $R_5$, $R_6$, $R_7$, and $R_8$ may be fused into a 2 to 5-membered fused ring.

The organometallic complex of Formula 2 may be represented by one of Formulas 3 through 6, but is not limited thereto.

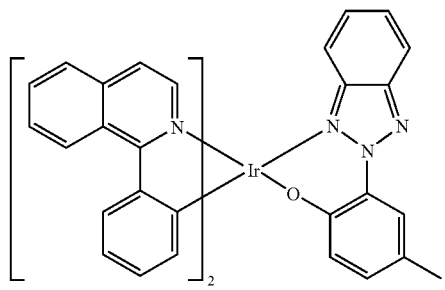

<Formula 3>

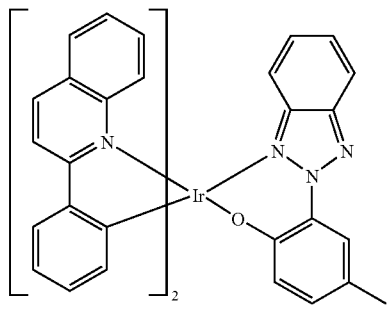

<Formula 4>

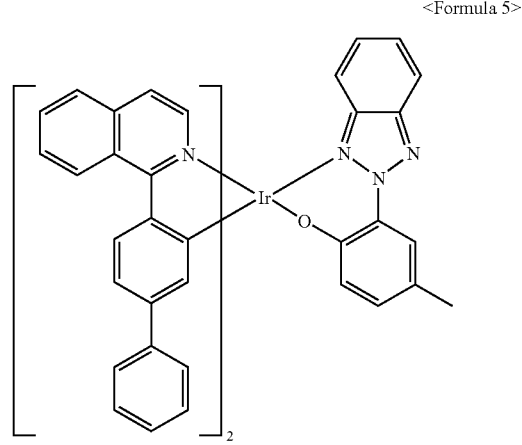

<Formula 5>

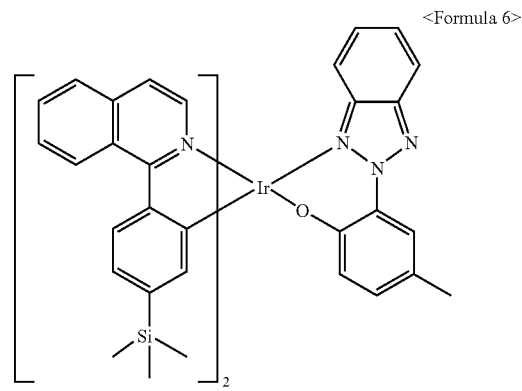

<Formula 6>

The organometallic complex represented by Formula 1 can be synthesized using a $[Ir(C{\char`\^}N)_2Cl]_2$ derivative, which is used as a starting material to provide a cyclometalating moiety, and a method disclosed by Watts Group (J.A.M.Chem.Soc. 1984, (106, 6647, which is incorporated herein by reference.)

An organic electroluminescence device of the embodiment of the present invention is manufactured by using the organometallic complex represented by Formula 1 to form an organic layer, for example, a light-emitting layer. The organometallic complex represented by Formula 1 is suitable as a phosphorescent dopant material for forming a light-emitting layer and exhibits excellent light emission of light of wavelengths corresponding to red light.

When the organometallic complex represented by formula 1 is used as the phosphorescent dopant, the organic layer may further include at least one host selected from the group consisting of one kind of polymer host, a mixture host of one or more kind of polymer host, a mixture host of a polymer and a small molecule, a small molecule host, and a non-emitting polymer matrix. Here, for polymer host, small molecule host, and non-emitting polymer matrix, any materials conventionally used to form a light emitting layer of an organic electroluminescent device can be used. Examples of the polymer host are, but are not limited to, poly(vinylcarbazole) (PVK), polyfluorene, and the like. Examples of the small molecule host are, but are not limited to, CBP(4,4'-N,N'-dicarbazole-biphenyl), 4,4'-bis[9-(3,6-biphenylcarbazolyl)]-1,1'-biphenyl, 9,10-bis[(2',7'-t-butyl)-9',9"-spirobifluorenyl anthracene, tetrafluorene, and the like. Examples of the non-emitting polymer matrix are, but are not limited to, polymethylmethacrylate, polystyrene, and the like.

The organometallic complex represented by Formula 1 may be in an amount of 1 to 30 parts by weight based on 100 parts by weight of materials used to form the light-emitting layer. When the amount is below 1 part by weight, phosphorescent materials are insufficient and thus, efficiency and lifetime are reduced. When the amount is above 30 parts by weight, quenching of triplet excitons occurs and thus, efficiency is reduced. In addition, when introducing the organometallic complex to form the light-emitting layer, various methods such as vacuum depositing, sputtering, printing, coating, and ink jetting can be used.

Moreover, the organometallic complex represented by Formula 1 may be used together with using green phosphorescent materials or blue phosphorescent materials to realize white light.

FIGS. 1a through 1f are diagrams schematically illustrating various laminated structures of an organic electroluminescent (EL) device according to embodiments of the present invention.

Referring to FIG. 1a, an organic electroluminescent device according to an embodiment of the present invention comprises a light emitting layer 12 having an organometallic complex of Formula 1 laminated on a first electrode 10 and a second electrode 14 formed on the light emitting layer 12.

Figure 1B:
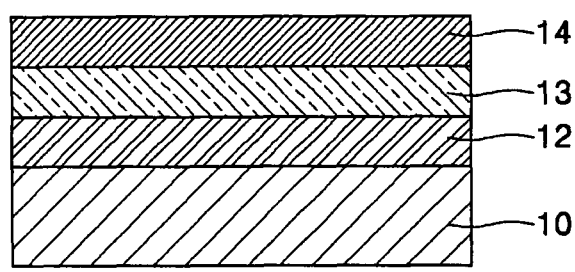

Referring to FIG. 1b, the organic electroluminescent device according to another embodiment of the present invention comprises a light emitting layer 12 having an organometallic complex of Formula 1 laminated on a first electrode 10, a hole blocking layer (HBL) 13 laminated on the light emitting layer 12, and a second electrode 14 formed on the HBL 13.

Figure 1C:
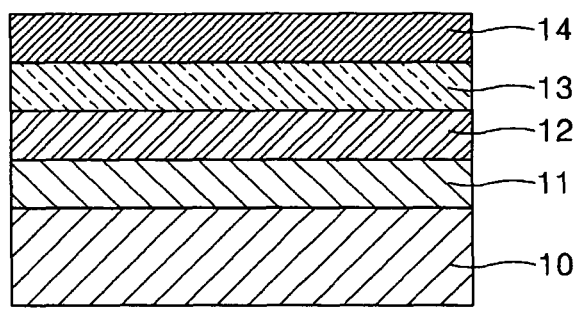

Referring to FIG. 1c, the organic electroluminescent device according to another embodiment of the present invention has the same structure as the embodiment shown in FIG. 1b except that a hole injection layer (HIL) 11 is further formed between the first electrode 10 and the light emitting layer 12.

Figure 1D:
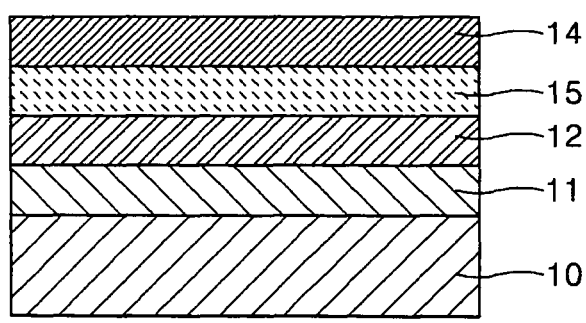

Referring to FIG. 1d, the organic electroluminescent device according to another embodiment of the present invention has the same structure as the embodiment shown in FIG. 1c except that an electron transport layer (ETL) 15 is formed on the light-emitting layer 12, instead of the HBL 13.

Figure 1E:
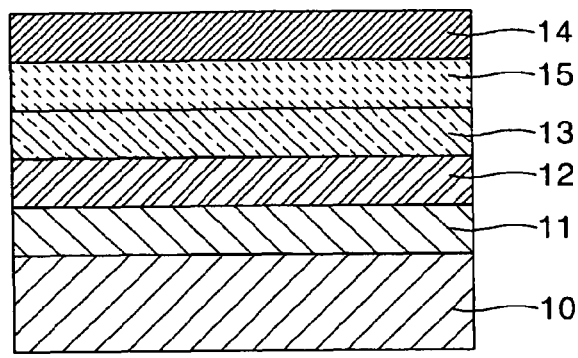

Referring to FIG. 1e, the organic electroluminescent device according to another embodiment of the present invention has the same structure as the embodiment shown in FIG. 1c except that a two-layer layer which includes the HBL 13 and the ETL 15 instead of the single layered HBL 13 is formed on the light emitting layer 12 having a biphenyl derivative of Formula 1, wherein the HBL 13 and the ETL 15 are sequentially laminated on the light emitting layer 12. In some cases, in FIG. 1e, an electron injection layer may be further formed between the ETL 15 and the second electrode 14.

Figure 1F:
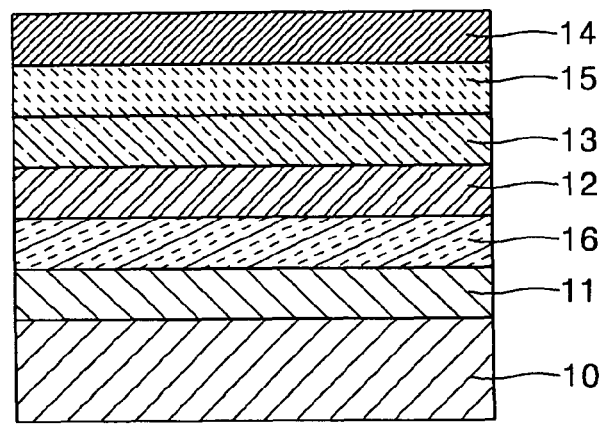

Referring to FIG. 1f, the organic electroluminescent device according to another embodiment of the present invention has the same structure as the embodiment shown in FIG. 1e except that a hole transport layer 16 is further formed between the HIL 11 and the light emitting layer 12. The hole transport layer 16 prevents impurities from penetrating into the light emitting layer 12 from the HIL 11.

The organic EL device having the laminated structures described above may be formed using conventional manufacturing methods, and the structures thereof are not particularly restricted.

The thickness of the organic layer may be in the range of 30 to 100 nm. When the thickness of the organic layer is below 30 nm, efficiency and lifetime thereof are reduced. When the thickness of the organic layer is above 100 nm, operating voltage is increased.

Here, the organic layer refers to a layer formed of organic compounds, which is formed between a pair of electrodes in an organic EL device, for example, a light emitting layer, an electron transport layer, and a hole transport layer.

In the organic EL device, a buffer layer may be interposed between each layer. The buffer layer may be formed of any materials used conventionally, for example, copper phthalocyanine, polythiophene, polyaniline, polyacetylene, polypyrrole, polyphenylene vinylene, or derivatives thereof, but is not limited thereto.

The HTL may be formed of any materials used conventionally, for example, polytriphenylamine, but is not limited thereto.

The ETL may be formed of any materials used conventionally, for example, polyoxadiazole, but is not limited thereto.

The HBL may be formed of any materials used conventionally, for example, LiF, $BaF_2$, or $MgF_2$, but is not limited thereto.

In the manufacture of the organic EL device of the embodiment of the present invention, special equipment and method are not required. The organic EL device can be manufactured according to conventional manufacturing methods using phosphorescent materials.

The organometallic complex of Formula 1 according to the embodiment of the present invention may emit light of a wavelength in the range of 550 to 650 nm.

A light emitting diode using the organometallic complex can be used in light source illuminations for full-color displays, backlights, outdoor billboards, optical communication, interior decoration, and so on.

The present invention will now be described in greater detail with reference to the following examples. The following examples are for illustrative purposes and are not intended to limit the scope of the invention.

Reference Example 1

Synthesis of 1-phenylisoquinoline iridium dimer

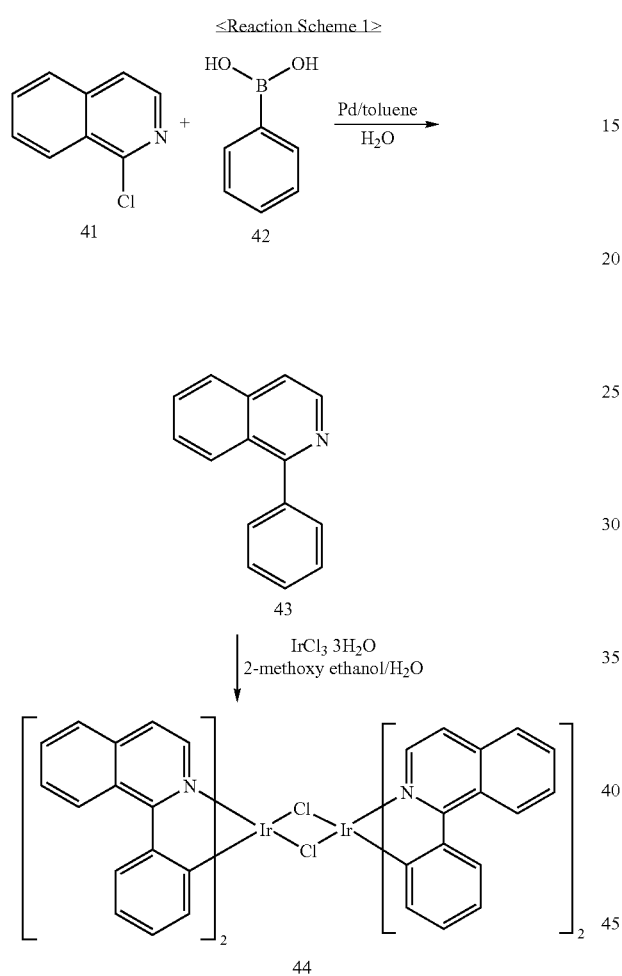

As illustrated in Reaction Scheme 1, a 2M sodium carbonate solution prepared with 95 ml of water, 5 g (31 mmol) of 1-chloroisoqinoline of Formula 41, 4.3 g (34 mmol) of phenyl boronic acid of Formula 42, 100 ml of toluene, and 48 ml of ethanol was added to a 500 ml branched flask and stirred in a nitrogen atmosphere at room temperature. Subsequently, 4.53 g (3.92 mmol) of tetrakis(triphenylphosphine)palladium (0) was added to the reaction mixture and refluxed in the nitrogen atmosphere in complete darkness for 15 hours.

After the reaction was completed, the reaction mixture was adjusted to room temperature and extracted using ethylacetate and water. The extracted resultant was separated using column chromatography (toluene:hexane=10:1), thereby obtaining a white solid (1-phenylisoqinoline of Formula 43) compound after the solvent evaporation.

A deep red powder 1-phenylisoquinoline iridium dimer of Formula 44 was prepared using the 1-phenylisoquinoline monomer and $IrCl_3 \cdot 3H_2O$. In this case, a synthesis method disclosed in J. Am. Chem. Soc., 1984, 106, 6647-6653, which is incorporated herein by reference, was used. The red powder was analyzed using a $^1H$ NMR spectrum:

$^1$H-NMR(CD$_2$Cl$_2$,ppm): 9.04 (d, 1H0, 8.96 (d, 1H), 8.12 (d, 1H), 7.83 (d, 2H), 7.78 (t, 2H), 6.82 (t,1H), 6.55 (d, 1H), 6.50 (t, 1H), 6.03 (d, 1H).

Reference Example 2

Synthesis of 2-phenylquinoline iridium dimer

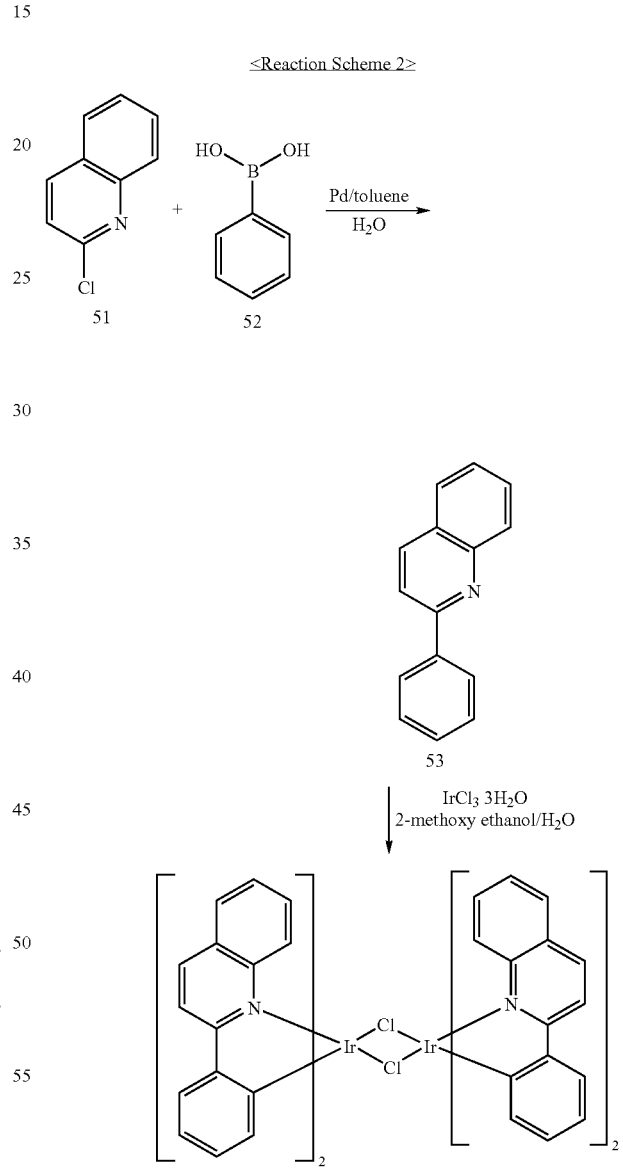

As illustrated in Reaction Scheme 2, a 2-phenylquinoline iridium dimer of Formula 54 was synthesized in the same manner as in Reference Example 1, except that 5 g (31 mmol) of 2-chloroquinoline of Formula 51 was used instead of 1-chloroisoquinoline.

Reference Example 3

Synthesis of 1-biphenylisoquinoline iridium dimer

Reference Example 4

Synthesis of 4'-trimethylsilyl-phenylisoquinoline iridium dimer

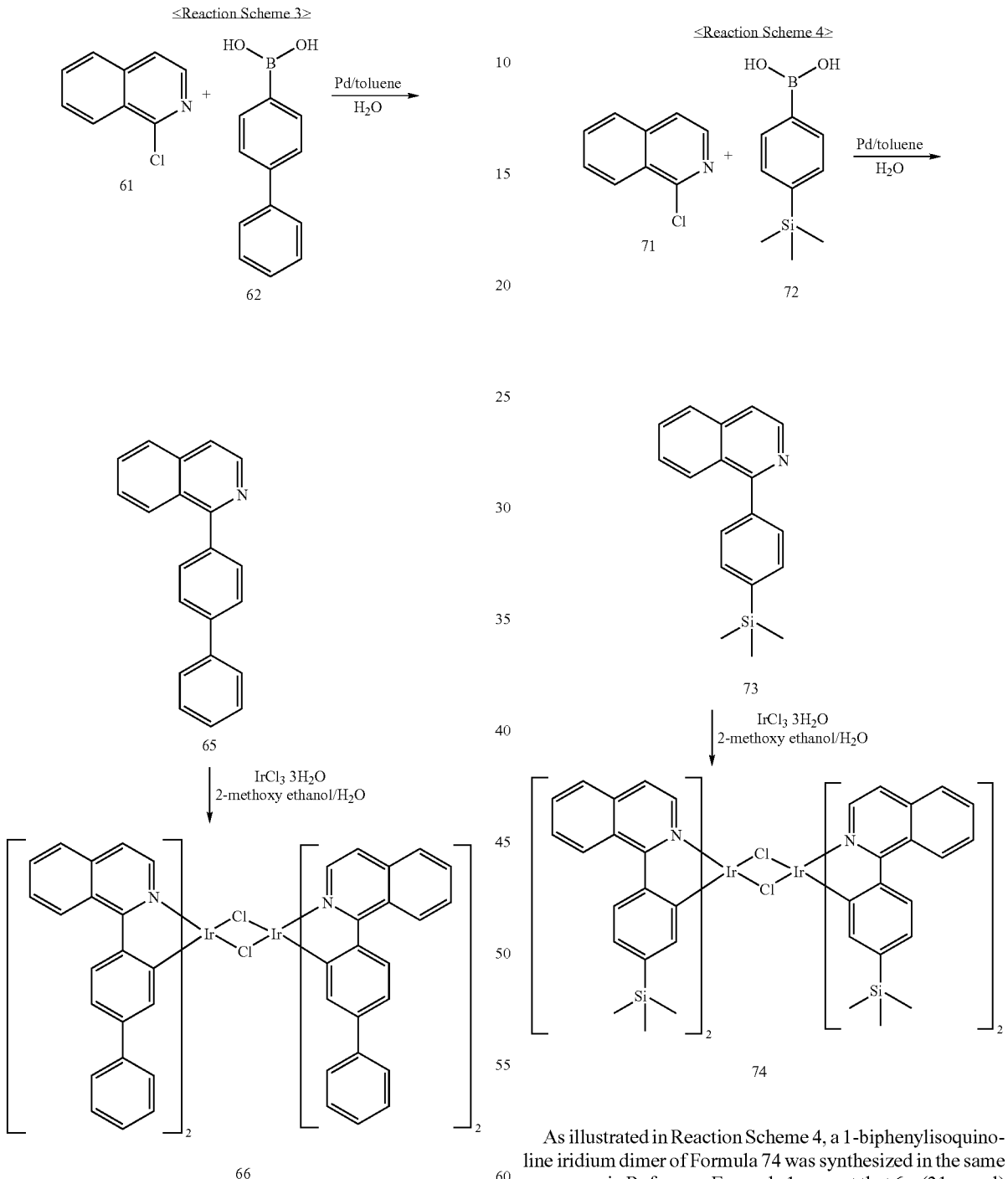

As illustrated in Reaction Scheme 3, a 1-biphenylisoquinoline iridium dimer of Formula 66 was synthesized in the same manner as in Reference Example 1, except that 6.1 g (31 mmol) of 4,4'-biphenyl boronic acid was used instead of phenylboronic acid.

As illustrated in Reaction Scheme 4, a 1-biphenylisoquinoline iridium dimer of Formula 74 was synthesized in the same manner as in Reference Example 1, except that 6 g (31 mmol) of 4'-silylphenyl boronic acid was used instead of phenylboronic acid. The product of reaction scheme 4 was analyzed using a $^1$H NMR spectrum:

$^1$H NMR (CDCl$_3$, ppm): 9.47 (d, 1H), 8.95 (d, 1H), 8.05 (d, 1H), 7.91 (d, 1H), 7.81-7.72 (m, 2H), 6.95 (t, 1H), 6.05 (s, 1H), −0.26 (9H, trimethylsilyl group).

Example 1

Synthesis of Compound Represented by Formula 3

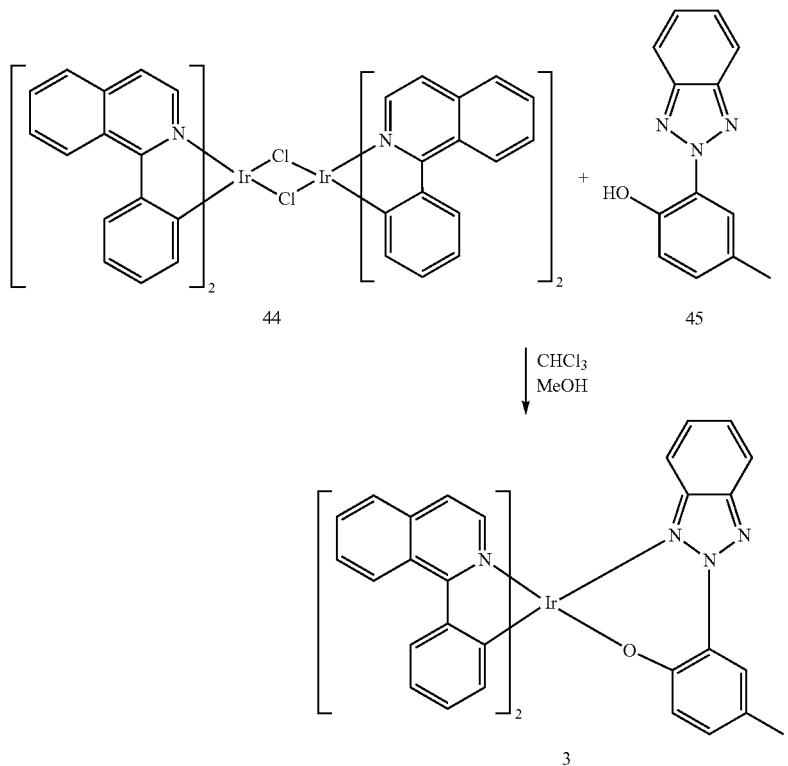

0.4 mmol of [Ir(1-phenylisoquinoline)$_2$Cl]$_2$ of Formula 44 and 0.88 mmol of 3-(2H-benzotriazole-2-yl)-4-hydroxyphenyl methane of Formula 45 and 2.0 mmol of sodium carbonate were added to a 250 ml branched flask and dissolved in 40 ml of trichloromethane and 15 mL of methanol to react in a nitrogen atmosphere at room temperature for 2 to 10 hours. After the reaction was completed, the reaction solution was Celite filtered and precipitated in hexane to obtain triazole phenolate represented by Formula 3. The obtained red solid was refined using silica gel column (methylene chloride: acetone=10:1). The structure of the final product was analyzed using a $^1$H NMR spectrum:

$^1$H-NMR(CD$_2$Cl$_2$,ppm): 9.07 (t, 2H), 8.90 (d, 1H), 8.41 (d, 1H), 8.11 (d, 1H), 7.93 (d, 1H), 7.85 (t, 2H), 7.75-7.61 (m, 5H), 7.33 (1H), 7.15 (t, 1H), 7.05 (d, 1H), 6.99 (d, dH), 6.92 (t, 1H), 6.90-6.65 (m, 4H), 6.47 (d, 1H), 6.29 (d, 1H), 6.13 (d, 1H), 6.06 (d, 1H), 2.25 (s, 3H, methyl group).

Example 2

Synthesis of Compound Represented by Formula 4

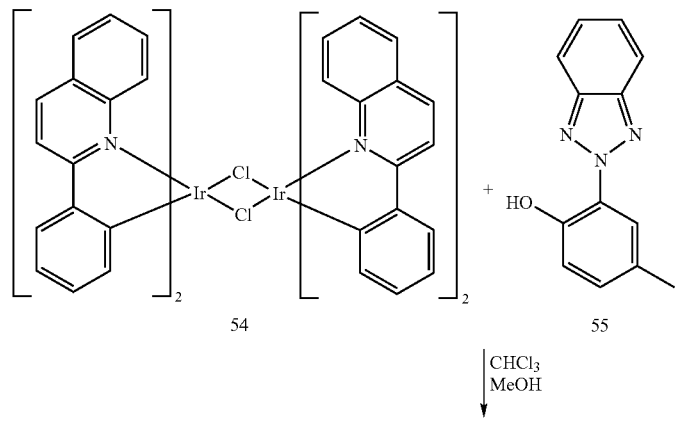

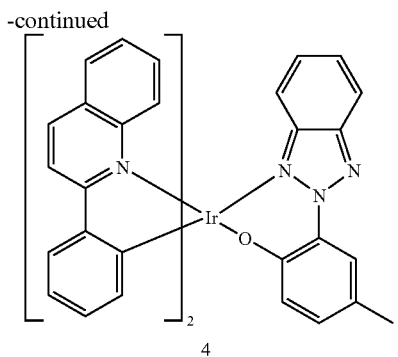
4
The compound represented by Formula 4 was synthesized in the same manner as in Example 1, except that a 2-phenylquinoline iridium dimmer of Formula 54 was used instead of a 1-phenylisoquinoline iridium dimer.
Example 3
Synthesis of Compound Represented by Formula 5
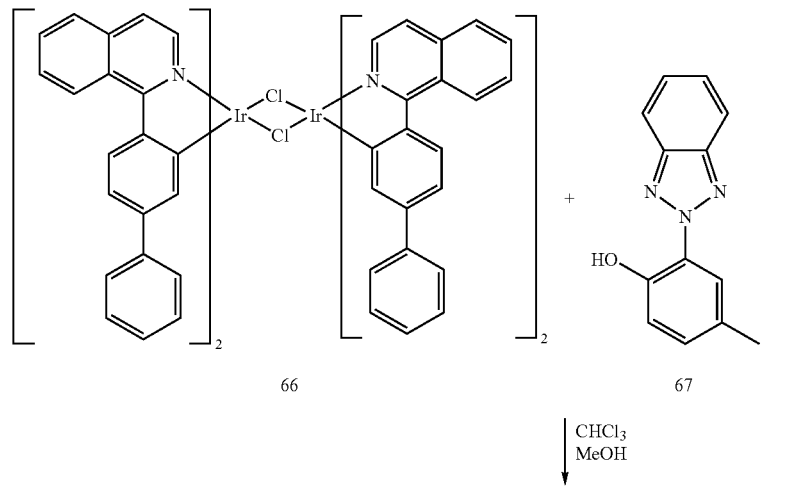
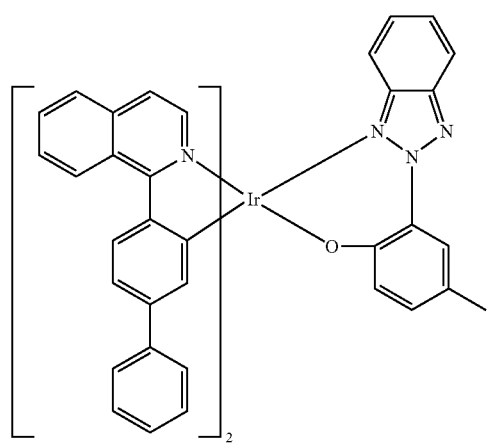
5

The compound represented by Formula 5 was synthesized in the same manner as in Example 1, except that a 1-biphenylisoquinoline iridium dimer of Formula 66 was used instead of a 1-phenylisoquinoline iridium dimer.

Example 4

Synthesis of Compound Represented by Formula 6

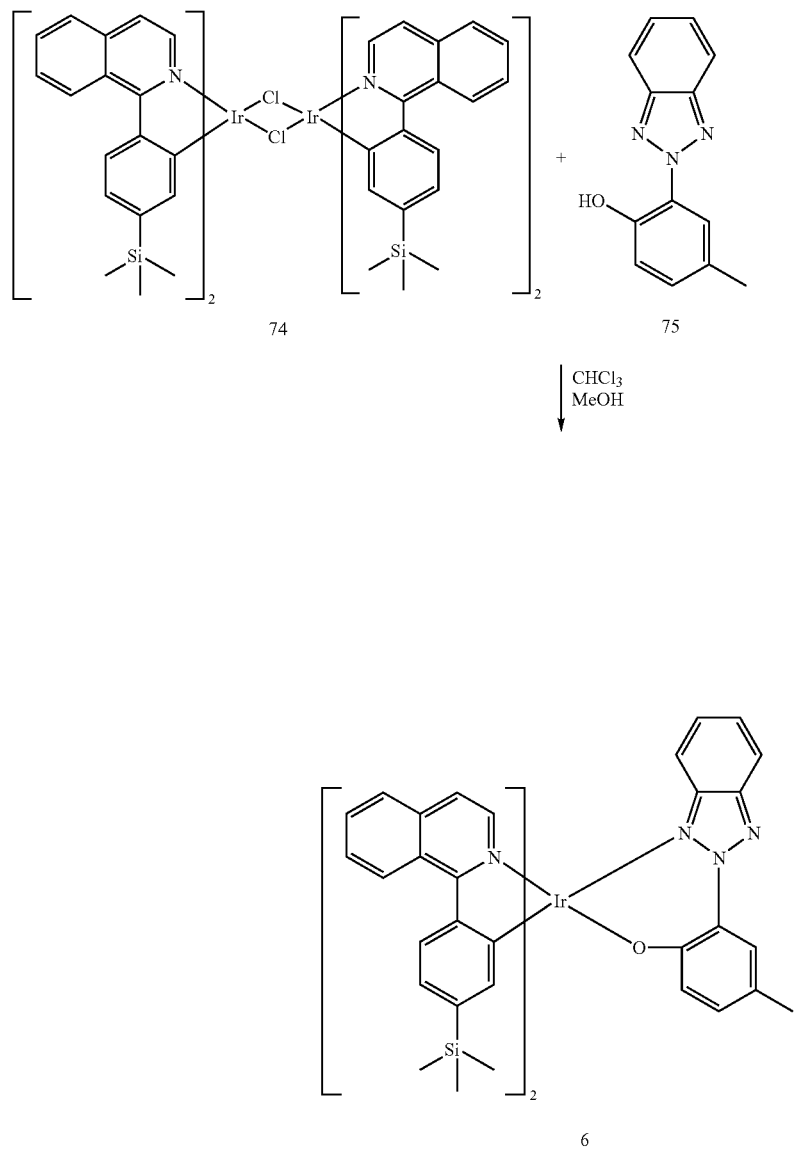

The compound represented by Formula 6 was synthesized in the same manner as in Example 1, except that a 1-(4'-trimethylsilyl)phenylisoquinoline iridium dimer of Formula 74 was used instead of a 1-phenylisoquinoline iridium dimer. The structure of the final product was identified using a $^1$H NMR spectrum:

$^1$H-NMR(CDCl$_3$,ppm): 9.05 (m, 2H), 8.87 (d, 1H), 8.30 (d, 1H), 8.03 (t, 2H), 7.90(t, 2H), 7.78-7.72 (m, 3H), 7.67-7.64 (m, 3H), 7.39 (d, 1H), 7.17(d, 2H), 7.04 (t, 2H), 6.88 (s, 1H), 6.79 (t, 1H), 6.54 (d, 1H), 6.30 (d, 1H), 5.98 (s, 1H), 5.81 (d, 1H), 2.17 (s, 3H methyl group), −0.11 (s, trimethylsilyl group), −0.28 (s, 9H trimethylsilyl group).

The compounds represented by Formulas 3 through 6 obtained according to Examples 1 through 4 were dissolved in methylene chloride to prepare 10$^{-4}$ M solutions, and photoluminescence characteristics of these solutions were measured. In addition, such solutions were spin coated on neat films and photoluminescence characteristics of the coated films were measured.

The photoluminescence characteristics and color coordinates (CIE) of the compounds represented by Formulas 3 to 6 which are obtained as shown in Examples 1 to 4 are shown in Table 1:

TABLE 1
| | PL characteristic $\lambda_{max}$ (nm) | | CIE (x, y) | |
|---|---|---|---|---|
| | Solution | Film | Solution | Film |
| Example 1: | 617 | 631 | (0.65, 0.34) | (0.67, 0.32) |
| Example 2: | 595 | — | (0.58, 0.41) | — |
| Example 3 | 632 | — | (0.68, 0.31) | — |
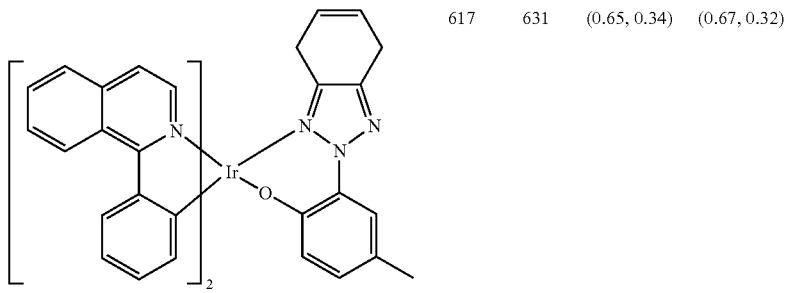
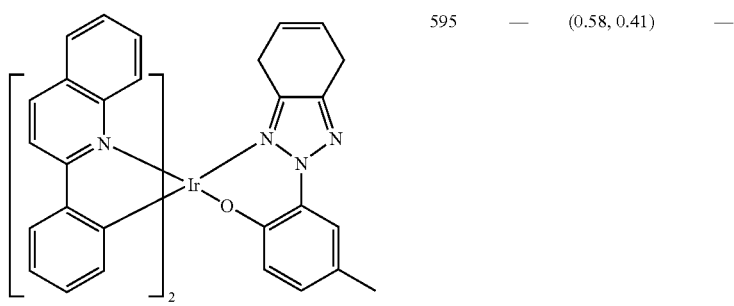
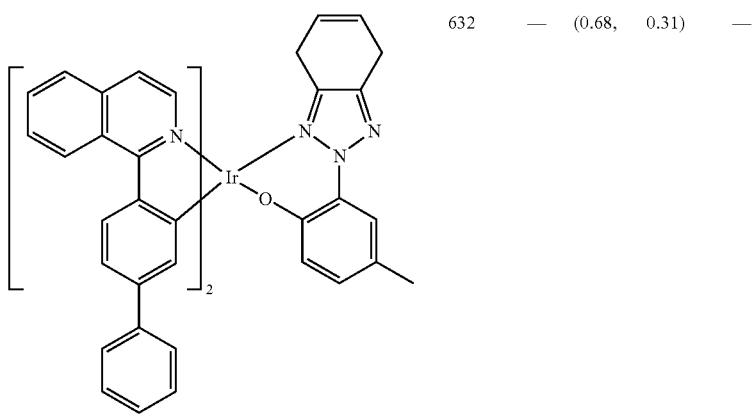

TABLE 1-continued

|  | PL characteristic $\lambda_{max}$ (nm) | | CIE (x, y) | |
|---|---|---|---|---|
|  | Solution | Film | Solution | Film |
| Example 4 | 634 | — | (0.68, 0.31) | — |

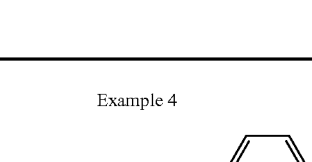

As illustrated in Table 1, dopants containing a triazole derivative used as an ancillary ligand having excellent phosphorescent characteristics are formed. In particular, the introduction of the substituent results in a strong electronic effect, and thus, the dopant is suitable to be used to form a phosphorescent material that emits light of a wavelength corresponding to red light.

Fabrication of Organic Electroluminescent (EL) Devices

Example 5

An indium-tin oxide (ITO)-coated transparent electrode substrate was washed and an ITO electrode pattern was formed on the substrate using a photoresist resin and an etchant. The ITO electrode patterned substrate was again washed. PEDOT{poly(3,4-ethylenedioxythiophene)}[Al 4083]-PSS was coated on the washed ITO electrode patterned substrate to a thickness of about 50 nm and baked at 120° C. for about 5 minutes to form a hole injection layer.

A mixture solution which was prepared by mixing PVK, CBP (PVK:CBP=4:5) and 8% by weight of the dopant of Formula 5 with chloroform was spin coated on the hole injection layer to form a light emitting layer with a thickness of 85 nm. Then, aluminum(III)bis(2-methyl-8-quinolinato)$_4$-phenylphenolate (Balq) was vacuum deposited to a thickness of 20 nm on the polymer light emitting layer using a vacuum deposition device under a pressure of $4 \times 10^{-6}$ torr or less and tris-8-hydroxyquinoline aluminum (Alq$_3$) was vacuum deposited to form an electron transport layer with a thickness of 15 nm. Then, LiF was vacuum deposited on the electron transport layer at a speed of 0.1 nm/sec to form an electron injection layer with a thickness of 1 nm.

Figure 2:
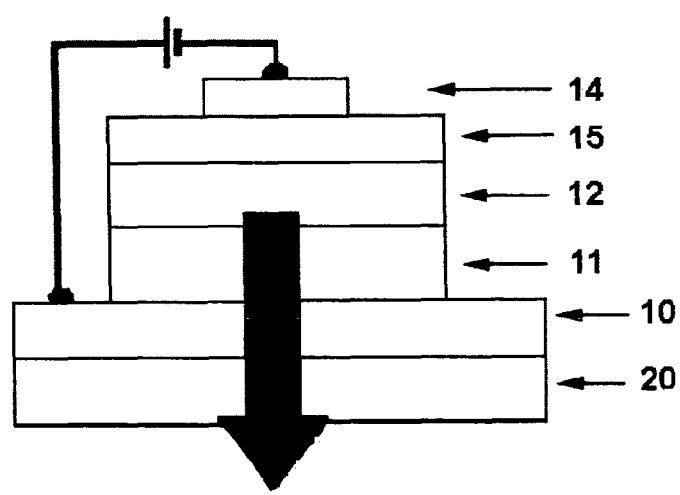
FIG. 2 is a diagram illustrating an organic electroluminescent device manufactured according to an embodiment of the present invention.

Subsequently, Al was deposited at a speed of 10 Å/sec to form an anode with a thickness of 150 nm and the resultant structure was encapsulated, thereby completing manufacture of the organic EL device. Here, the encapsulating process was performed by sealing the resultant structure of the Al deposition in a glove box in which BaO powder was present in a dry nitrogen gas atmosphere and by final treating using UV hardener. The structure of the device is ITO/PEDOT-PSS (50 nm)/PVK-CBP (4:5)-dopant 8% by weight (85 nm)/Balq (20 nm)/Alq$_3$ (15 nm)/LiF (1 nm)/Al (150 nm). The organic EL device had a multi-layer structure and its schematic view is illustrated in FIG. 2. In this case, the light emitting area of the organic EL device was 6 mm$^2$.

Example 6

An organic EL device was manufactured in the same manner as in Example 5, except that the compound represented by Formula 4 was used instead of the compound represented by Formula 5.

Example 7

An organic EL device was manufactured in the same manner as in Example 5, except that the compound represented by Formula 3 was used instead of the compound represented by Formula 5.

Example 8

An organic EL device was manufactured in the same manner as in Example 5, except that the compound represented by Formula 6 was used instead of the compound represented by Formula 5 (synthesized in Example 1).

Comparative Example

An organic EL device was manufactured in the same manner as in Example 5, except that the compound of Formula 7 was used instead of the compound represented by Formula 3.

<Formula 7>

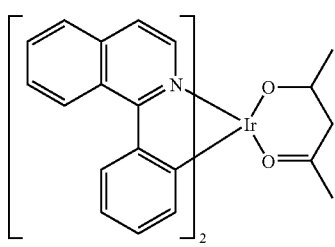

The photoluminescence characteristics, color coordinates (CIE), current efficiency, operating voltage, and brightness of the compounds of Example 5 and Comparative Example are shown in Table 2.

TABLE 2

| | EL $\lambda_{max}$ (nm) | CIE (x, y) | Current efficiency Cd/A | Operating voltage (V) | Maximum brightness (cd/m$^2$) |
|---|---|---|---|---|---|
| Example 5 | 620 | (0.66, 0.32) | 5.48 at 6.61 mA/cm$^2$ and 10 V | 5.5 | 4541 at 13.5 V |
| Comparative Example | 628 | (0.68, 0.31) | 3.5 at 1.69 mA/cm$^2$ and 13 V | 7.5 | 2690 at 21.5 V |

As illustrated in Table 2, the organic electroluminescent device of Example 5 including the compound represented by Formula 3 of the embodiment of the present invention shows high brightness in a wavelength corresponding to red light emitting region and high current density even at a low voltage, and can operate even at a relatively low voltage.

An organometallic complex according to the embodiment of the present invention can effectively emit light of a wavelength corresponding to red light. The organometallic complex is suitable to form an organic layer of an organic EL device, and efficiently emits light in a wavelength range of 550 to 650 nm as efficient phosphorescent materials. In addition, when the organometallic complex is used with a green phosphorescent material or a blue phosphorescent material, white light can be realized.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An organometallic complex comprising a compound represented by one selected from the group consisting of Formulae 3-6:

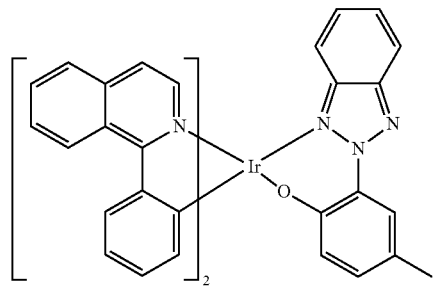
(3)

-continued

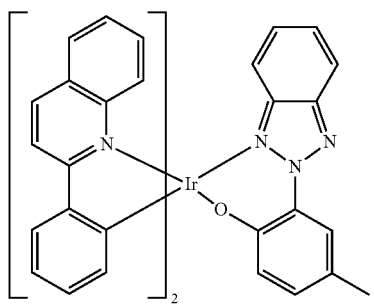
(4)

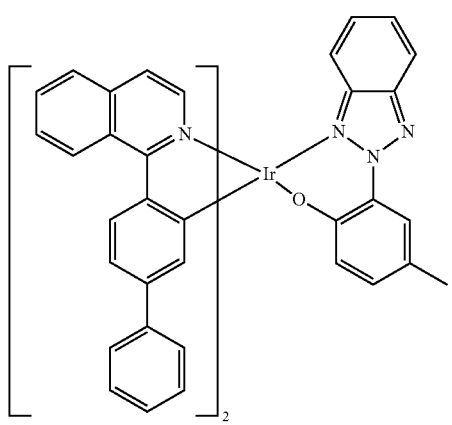
(5)

4. The organometallic complex of claim 1, wherein the compound is represented by Formula 5:

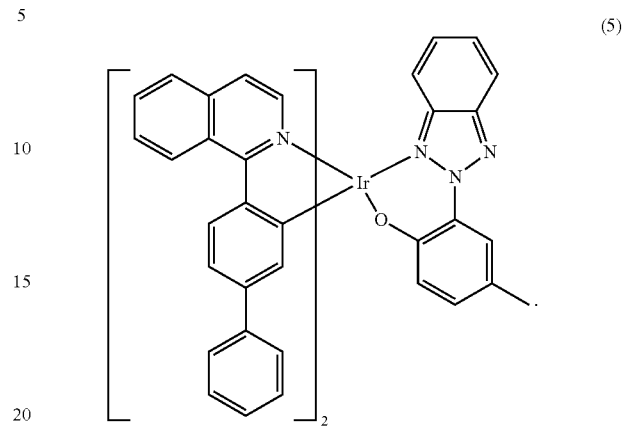
(5)

5. The organometallic complex of claim 1, wherein the compound is represented by Formula 6:

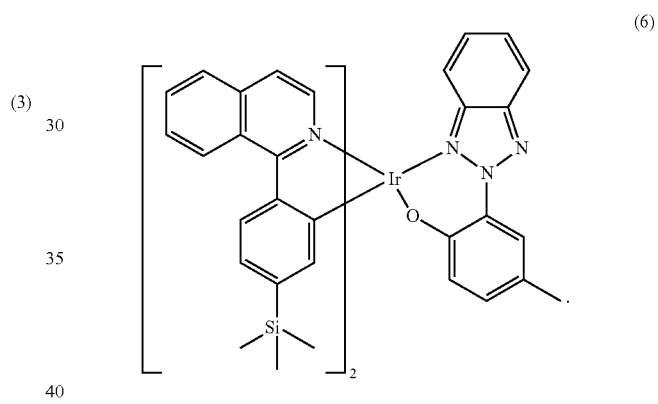
(6)

2. The organometallic complex of claim 1, wherein the compound is represented by Formula 3:

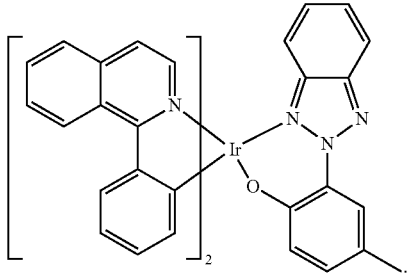
(3)

3. The organometallic complex of claim 1, wherein the compound is represented by Formula 4:

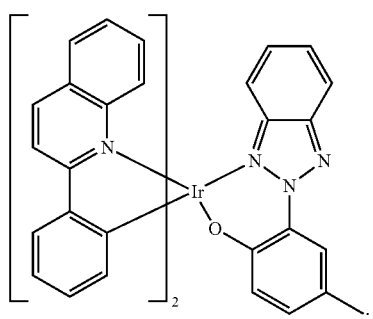
(4)

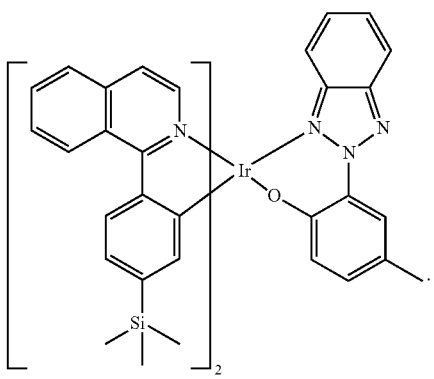
(6)

6. An organic electroluminescence device having an organic layer interposed between a pair of electrodes, the organic layer comprising the organometallic complex of claim 1.

7. An organic electroluminescence device, comprising:
a first electrode;
a second electrode; and
an organic layer comprising a light emitting layer comprised of an organometallic complex represented by one of Formulae 3 through 6:

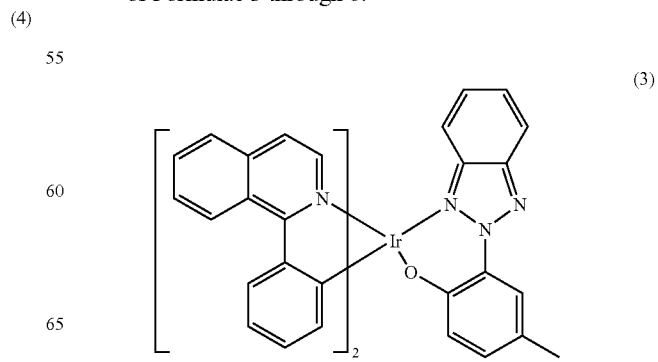
(3)

-continued (4)

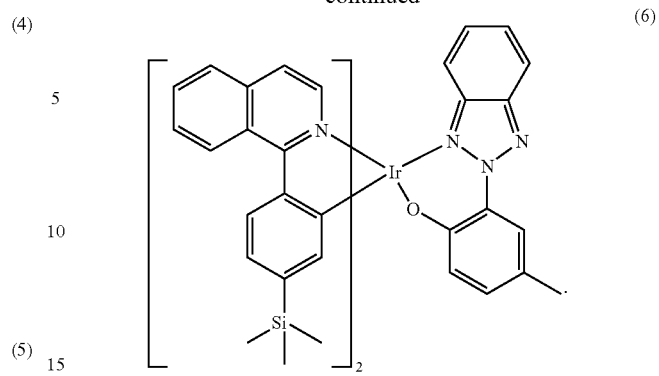

(5)

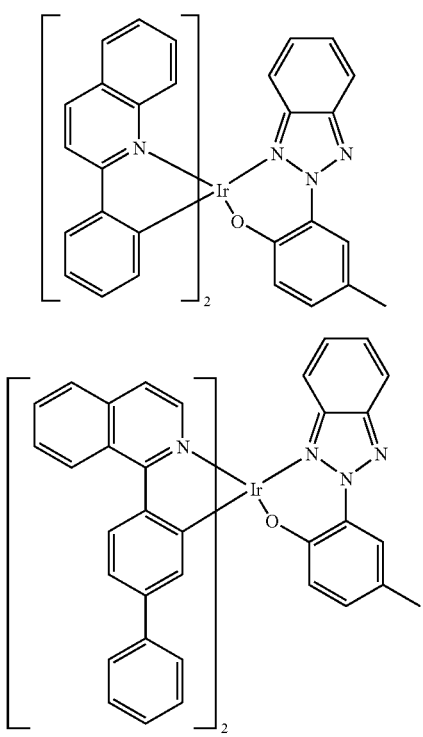

(6)

8. The organic electroluminescence device of claim 7, wherein the organometallic complex is in an amount of 1 to 30 parts by weight based on 100 parts by weight of materials used to form the light emitting layer.

9. The organic electroluminescence device of claim 7, wherein the organic layer further comprises at least one host selected from the group consisting of one kind of polymer host, a mixture host of one or more kinds of polymer host, a mixture host of a polymer and a small molecule, a small molecule host, and a non-emitting polymer matrix.

10. The organic electroluminescence device of claim 7, wherein the organic layer further comprises green phosphorescent materials or blue phosphorescent materials.

* * * * *